United States Patent
Grass et al.

(10) Patent No.: US 9,169,228 B2
(45) Date of Patent: Oct. 27, 2015

(54) 2,5-FURAN DICARBOXYLATES COMPRISING ISODECANOLS, AND USE THEREOF

(75) Inventors: Michael Grass, Haltern am See (DE); Hinnerk Gordon Becker, Essen (DE)

(73) Assignee: EVONIK DEGUSSA GmbH, Essen (DE)

( * ) Notice: Subject to any disclaimer, the term of this patent is extended or adjusted under 35 U.S.C. 154(b) by 654 days.

(21) Appl. No.: 13/393,120

(22) PCT Filed: Jul. 30, 2010

(86) PCT No.: PCT/EP2010/061123
§ 371 (c)(1),
(2), (4) Date: Apr. 30, 2012

(87) PCT Pub. No.: WO2011/023491
PCT Pub. Date: Mar. 3, 2011

(65) Prior Publication Data
US 2012/0202725 A1 Aug. 9, 2012

(30) Foreign Application Priority Data
Aug. 28, 2009 (DE) .......................... 10 2009 028 976

(51) Int. Cl.
| C08K 5/1535 | (2006.01) |
| C08K 5/10 | (2006.01) |
| C08F 14/06 | (2006.01) |
| C10M 129/72 | (2006.01) |
| C09D 11/00 | (2014.01) |
| C07D 307/68 | (2006.01) |
| C09D 11/033 | (2014.01) |

(52) U.S. Cl.
CPC .............. *C07D 307/68* (2013.01); *C08K 5/10* (2013.01); *C08K 5/1535* (2013.01); *C09D 11/033* (2013.01); *C10M 129/72* (2013.01); *C10M 2207/282* (2013.01); *C10M 2207/285* (2013.01); *C10M 2207/2825* (2013.01); *C10M 2207/2855* (2013.01)

(58) Field of Classification Search
None
See application file for complete search history.

(56) References Cited

U.S. PATENT DOCUMENTS

| 3,259,636 A * | 7/1966 | Lew ............................... 549/485 |
| 6,355,711 B1 * | 3/2002 | Godwin et al. ............... 524/285 |
| 7,786,201 B2 | 8/2010 | Grass et al. |
| 7,964,658 B2 | 6/2011 | Grass |
| 8,022,244 B2 | 9/2011 | Grass et al. |
| 8,258,325 B2 | 9/2012 | Grass et al. |
| 2007/0060768 A1 * | 3/2007 | Grass et al. .................... 560/103 |
| 2007/0179229 A1 * | 8/2007 | Grass ............................ 524/287 |
| 2008/0188601 A1 * | 8/2008 | Grass et al. .................... 524/321 |
| 2008/0245996 A1 * | 10/2008 | Grass et al. ............. 252/182.12 |
| 2009/0301348 A1 * | 12/2009 | Grass et al. ................ 106/287.2 |
| 2010/0305255 A1 | 12/2010 | Grass |
| 2012/0202725 A1 * | 8/2012 | Grass et al. .................... 508/308 |
| 2012/0220507 A1 * | 8/2012 | Grass et al. .................... 508/309 |
| 2014/0128623 A1 * | 5/2014 | Janka et al. .................... 549/485 |

OTHER PUBLICATIONS

U.S. Appl. No. 13/392,974, filed Feb. 28, 2012, Grass, et al.
U.S. Appl. No. 14/008,425, filed Sep. 27, 2013, Becker, et al.
U.S. Appl. No. 14/001,177, filed Aug. 23, 2013, Becker, et al.
U.S. Appl. No. 14/001,597, filed Oct. 8, 2013, Becker, et al.
U.S. Appl. No. 14/001,338, filed Sep. 5, 2013, Becker, et al.
Sanderson, R.D., et al., "Synthesis and Evaluation of Dialkyl Furan-2,5-Dicarboxylates as Plasticizers for PVC," Journal of Applied Polymer Science, vol. 53, No. 13, pp. 1785-1793, (Sep. 26, 1994).
International Search Report Issued Oct. 21, 2010 in PCT/EP10/61123 Filed Jul. 30, 2010.

* cited by examiner

*Primary Examiner* — Joseph D Anthony
(74) *Attorney, Agent, or Firm* — Oblon, McClelland, Maier & Neustadt, L.L.P.

(57) ABSTRACT

The invention relates to mixtures of isodecyl furan-2,5-dicarboxylate of formula I, methods for producing said mixtures of isodecyl furan-2,5-dicarboxylate of formula I, compositions containing mixtures of isodecyl furan-2,5-dicarboxylate of formula I, uses of the mixtures of isodecyl furan-2,5-dicarboxylate of formula I as plasticizers, and uses of the aforementioned compositions containing isodecyl furan-2,5-dicarboxylate of formula I.

17 Claims, No Drawings

2,5-FURAN DICARBOXYLATES COMPRISING ISODECANOLS, AND USE THEREOF

The present invention relates to a mixture of esters of 2,5-furandicarboxylic acid (FDCA) with C10 alcohols, more particularly mixtures of branched decanols. The present invention likewise relates to a process for preparing such esters and mixtures and to the use thereof as plasticizers for polymers such as polyvinyl chloride, for example.

Polyvinyl chloride (PVC) is among the most economically important polymers. It finds diverse applications both as unplasticized PVC and as plasticized PVC.

To produce a plasticized PVC, the PVC is admixed with plasticizers, for which in the great majority of cases esters of phthalic acid are used, more particularly di-2-ethylhexyl phthalate (DEHP), diisononyl phthalate (DINP), dipropylheptyl phthalate (DPHP), and diisodecyl phthalate (DIDP), but also the terephthalic acid derivative di-2-ethylhexyl terephthalate (DENT or DOTP). At the same time, for a number of years, the production of the C10 oxo-process alcohols, more particularly of 2-propylheptanol, has experienced a sharp increase, not least on account of the favorable raw-materials base, and it is likely that further capacity increases will follow. At the present time, the use of this alcohol as a starting material for plasticizers is confined almost exclusively to the corresponding phthalate, DIDP or DPHP. Although these are among the plasticizers referred to as standard plasticizers, their performance properties relative to DEHP, DINP and DOTP in the relatively important plastisol market means that they can be used only subject to relatively severe limitations, owing to the reduced gelling and the poorer plasticizing properties. It would be desirable, therefore, to have esters of isodecanol, preferably one with high 2-propylheptanol fractions, possessing properties such that they can be used not only in the conventional thermoplastic applications such as films, cable sheathing, and in some cases roofing sheets, but also, increasingly, in the plastisol applications.

On account of the limited availability of fossil raw materials, the associated likely future sharp price rises, and the increasingly vocal calls—from politicians among others—for use of renewable raw materials, such esters ought in particular to have good market opportunities in the future, with at least the acid component being based on naturally occurring resources such as sugars, fats or oils.

In the publication "Top Value Added Chemicals from Biomass" by T. Werpy and G. Petersen, 2,5-furandicarboxylic acid (FDCA) is regarded as one of the most promising platform chemicals on the basis of sugar. On account of its structural similarity with terephthalic acid, recent years have seen the publication of numerous papers on the use of 2,5-furandicarboxylic acid or various derivatives, primarily in polymers. The principal application in the majority of cases has been the partial or complete substitution of terephthalic acid or its derivatives in polymers. A very extensive review of FDCA, its applications, and its synthesis possibilities is found in the Internet publication by Jaroslaw Lewkowski, ARKIVOC 2001 (i), pages 17-54, ISSN 1424-6376, with the title "Synthesis, Chemistry and Applications of 5-hydroxymethylfurfural and its derivatives". Common to the majority of these syntheses is an acid-catalyzed reaction of carbohydrates, especially glucose or fructose, preferably fructose, to give 5-hydroxymethylfurfural (5-HMF), which can be isolated from the reaction medium by processing operations such as a two-phase regime, for example. Corresponding results have been described, for example, by Roman-Leshkov et al. in Science 2006, 312, pages 1933-1937, and by Zhang in Angewandte Chemie 2008, 120, pages 9485-9488.

In a further step, 5-HMF can then be oxidized to FDCA, as cited by Christensen in ChemSusChem 2007, 1, pp. 75-78, for example.

Also described, furthermore, is the preparation of certain FDCA esters by a direct synthesis starting from mucic acid (Tagouchi in Chemistry Letter vol. 37, No. 1 (2008)) and the corresponding alcohols.

The use of esters of 2,5-furandicarboxylic acid as plasticizers for plastics, more particularly PVC, PVB, PLA, PHB or PAMA, has not often hitherto been described. The most extensive review in this context is found in the publication by R. D. Sanderson et al. in Journal of Appl. Pol. Sci. 1994, vol. 53, pp. 1785 to 1793. Explicitly described there are the corresponding esters based on n-butanol, n-hexanol, 2-octanol, and 2-ethylhexanol. The investigations into the interaction of the esters with PVC show that they could absolutely be used as plasticizers for PVC. These conclusions, however, were derived only from DMTA measurements. Performance investigations, which are important and more meaningful for the processor, were not carried out.

Starting out from the known state of the art, therefore, the object was that of providing an ester based on an isodecanol, more particularly one with high fractions of 2-propylheptanol, and on an acid component based on renewable raw materials, that can be used as plasticizer for plastics such as PVC, PVB, PLA, PHB or PAMA, for example, and that exhibits significantly improved plastisol gelling and plasticizing effect as compared with DPHP, thereby significantly enlarging the application spectrum of the parent alcohol.

It has been found that mixtures of isomeric decyl esters of 2,5-furandicarboxylic acid (formula I) can be used as plasticizers for plastics, more particularly PVC, PVB, and PAMA, where they exhibit advantageous properties relative to the FDCA esters already known from the literature. Moreover, relative to the corresponding esters of phthalic acid such as DIDP or DPHP, these esters likewise exhibit performance advantages.

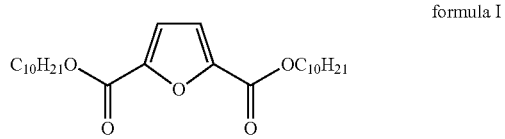

formula I

The present invention thus provides mixtures of isomeric decyl esters of 2,5-furandicarboxylic acid of the formula I. Further provided by the invention are compositions comprising the mixtures of isomeric decyl esters of 2,5-furandicarboxylic acid according to formula I.

The present invention further provides for the use of these mixtures in paints, inks or varnishes, in plastisols, adhesives or adhesives components, in sealants, as plasticizers in plastics or plastics components, as solvents, as a lubricating oil component and as an auxiliary in metals processing, and also provides a PVC composition or a plastisol comprising PVC and from 5 to 250 parts by mass of the mixture of the invention per 100 parts by mass of PVC.

The present invention also provides a process for preparing mixtures of isomeric decyl esters of 2,5-furandicarboxylic acid, characterized in that 2,5-furandicarboxylic acid is esterified with a mixture of isomeric decanols, called isodecanol below, optionally in the presence of a catalyst, or dimethyl 2,5-furandicarboxylate is transesterified with isodecanol, with release of methanol, optionally using a catalyst, to give the mixture of isomeric decyl esters of 2,5-furandicarboxylic acid. Furthermore, the ester mixture of the invention can also be obtained by first converting 2,5-furandicarboxylic acid into the dichloride, using chlorinating agents, and then reacting this dichloride with isodecanol to give the target product, with release of hydrogen chloride.

Furthermore, for preparing a mixture of isomeric decyl esters it is additionally possible to start from mucic acid as well, which, in the presence of isodecanols and with preferably acidic catalysis, is simultaneously—in a one-pot reaction—cyclized and reacted to give the corresponding furandicarboxylic diester.

Relative to prior-art furandicarboxylic esters, the mixtures of isomeric decyl esters of FDCA of the invention exhibit significantly improved properties in the context of their use as plasticizers in plastics, especially PVC.

Relative to the prior-art DPHP, the esters of the invention have an enhanced plasticizing effect (efficiency), a significantly improved gelling, with an at least comparable volatility. As against what has hitherto been the standard product for plastisol applications, DINP, the plasticizing effect observed is comparable, the gelling is only a little slower, and volatility is improved. As compared with DOTP, which has been used increasingly for some time on account of the phthalate debate, the esters of the invention exhibit improvements in gelling and in plasticizing effect.

The composition of the mixtures of isomeric decyl esters of 2,5-furandicarboxylic acid according to formula I, of the invention, is preferably such that the mixture of the esters has a high fraction of 2-propylheptyl radicals. It is advantageous if the mixture of the esters has a fraction of 2-propylheptyl radicals in the C10 side chain in a range from 50 up to a maximum of 99 mol %. It is advantageous, moreover, if the mixture of esters of the invention has less than 20 mol % of C10 side chains with quaternary C atoms.

The mixture of the invention may either consist exclusively of the diesters of the formula I or as well as these may comprise at least one polymer and/or at least one plasticizer which is not a diester of the formula I. These plasticizers may be selected, for example, from the trialkylesters of citric acid, acylated trialkylesters of citric acid, glycerol esters, glycol dibenzoates, alkyl benzoates, dialkyl adipates, trialkyl trimellitates, dialkyl terephthalates, dialkyl phthalates or the dialkyl esters of 1,2-, 1,3- or 1,4-cyclohexanedicarboxylic acids, the alkyl radicals having from 4 to 13, preferably 5, 6, 7, 8, 9, 10, 11 or 13, carbon atoms. The plasticizers may also be dianhydrohexitol esters, preferably isosorbide diesters of carboxylic acids, such as n- or isobutyric acid, valeric acid or 2-ethylhexanoic acid or isononanoic acid, for example.

Polymers which may be present in the mixture of the invention are, for example, polyvinyl chloride (PVC), polyvinylbutyral (PVB), polylactic acid (PLA), polyhydroxybutyral (PHB), and polyalkyl methacrylates (PAMA). With particular preference the polymer is polyvinyl chloride (PVC).

In preferred mixtures which comprise diesters of the formula I and polymers, the mass ratio of polymer/polymers to diester/diesters of the formula I is preferably from 30:1 to 1:2.5 and more preferably from 20:1 to 1:2.

In preferred mixtures comprising diesters of the formula I and plasticizers which are not a diester of the formula I, the molar ratio of plasticizers, more particularly of alkyl benzoates, dialkyl adipates, glycerol esters, trialkylesters of citric acid, acylated trialkylesters of citric acid, trialkyl trimellitates, glycol dibenzoates, dialkyl terephthalates, dialkyl phthalates, dialkanoyl esters of isosorbide and/or the dialkyl esters of 1,2-, 1,3- or 1,4-cyclohexanedicarboxylic acids, to diester/diesters of the formula I is preferably from 1:15 to 15:1, more preferably from 1:6 to 6:1.

The mixtures of diesters of the formula I of the invention, and the diesters of the formula I themselves, can be prepared in various ways. Preferably the mixtures of diesters of the formula I and/or the diesters of the formula I are prepared by the process described below.

The process of the invention for preparing isomeric decyl esters of 2,5-furandicarboxylic acid is distinguished by the fact that 2,5-furandicarboxylic acid or a relatively short-chain dialkyl ester of this compound, especially the dimethyl ester, is reacted with a mixture of isomeric decanols, with a catalyst being used optionally. Furthermore, the 2,5-furandicarbonyl dichloride which may be obtained by reacting the FDCA with chlorinating agents such as thionyl chloride, for example, can be used as a starting material for preparing diisodecyl esters. Suitable conditions for the reaction of FDCA to give the diisodecyl ester via the dichloride as intermediate are found in the examples.

It is preferred to use a mixture of isomeric decanols which contains 50-99 mol %, more particularly 70-99 mol %, more preferably 85-99 mol %, more particularly 95-99 mol % of 2-propylheptanol.

Preparation of the Isomeric Decyl Alcohols

In principle, all technical mixtures of decanols, especially primary alcohols and/or alcohol mixtures having the general empirical formula $C_{10}H_{21}OH$, can be used. It is preferred to use those mixtures of isomeric decanols with the formula $C_9H_{19}CH_2OH$ that in terms of the fraction of 2-propylheptanol or n-decanol, and also in terms of the amount of multiply substituted C10 alcohols with quaternary C atoms, are situated within the ranges indicated above. Particularly preferred are decanols having a high fraction of 2-propylheptanol.

The C10 alcohols which can be used for preparing the ester mixtures of the invention are easily obtainable technically by aldol condensation of the C5 aldehydes n-valeraldehyde (=n-pentanal), isovaleraldehyde (2-methylbutanal), and 3-methylbutanal, with subsequent water elimination and hydrogenation.

N- and isovaleraldehyde can be prepared in turn, for example, by hydroformylation of 1-butene or 2-butene. In this reaction, n- and isovaleraldehyde are obtained in varying proportions according to the hydroformylation catalyst used and the reaction conditions. Where such a mixture is subjected to aldol condensation, a variety of substituted products are obtained; the hydroformylation of isobutene provides access to 3-methylbutanal.

The isodecanols can be synthesized through the following steps:

a) a $C_4$ olefin or a $C_4$ olefin mixture is hydroformylated to give the corresponding $C_5$ aldehydes b) the aldehydes formed under a) are aldol-condensed to form decenals c) the decenals formed in step b) are hydrogenated to form decanols.

The decanol mixtures are prepared using 1-butene, 2-butenes, isobutene or mixtures of these olefins as starting materials. The hydroformylation of these mixtures can be carried out by a variety of processes.

Generally speaking, cobalt or rhodium catalysts, with or without modification, are used for the hydroformylation.

The hydroformylation of isobutene to 3-methylbutanal is described in, for example, the following reference (V. Y. Gankin, L. S. Genender, D. M. Rudkovskii, USSR Zh. Prikl. Khim. (Leningrad) (1968), 41 (10), pp. 2275-81).

The hydroformylation of linear butenes or mixtures thereof is disclosed in, for example, the publications EP 0 094 456, DE 196 17 178, EP 0 562 451 or EP 0 646 563.

The aldol condensation of n-valeraldehyde, isovaleraldehyde, 3-methylbutanal or a mixture of $C_5$ aldehydes takes place typically by exposure to basic catalysts. Catalysts employed include alkali metal carbonates or alkali metal hydroxides, more particularly compounds of sodium or potassium, or amines, preferably tertiary amines such as triethylamine, tri-n-propylamine, tri-n-butylamine. Operation takes place at temperatures of 60 to 160° C., more particularly 80 to 130° C., and at atmospheric pressure or at a pressure increased to approximately 1 MPa. The reaction time is a few minutes up to several hours, and is dependent in particular on catalyst type and reaction temperature.

The aldol condensation of $C_5$ aldehydes in stirred reactors is described in WO 93/20034, for example. The performance of aldol condensations on aldehydes in tube reactors is disclosed in DE 199 57 522, for example.

The decenals obtained by aldol condensation of the $C_5$ aldehydes are hydrogenated in pure form or as a mixture. The hydrogenation is preferably performed in the liquid phase.

For the hydrogenation it is possible to use catalysts or catalyst systems which hydrogenate not only olefinic double bonds but also carbonyl groups. Catalysts particularly suitable for the hydrogenation of the α,β-unsaturated aldehydes are those used in the art for the hydrogenation of 2-ethylhex-2-enal to 2-ethylhexanol.

For the hydrogenation it is possible to use, for example, copper/nickel, copper/chromium, copper/chromium/nickel, zinc/chromium, nickel/molybdenum catalysts. Combinations of two or more catalysts can be used as well. The catalysts may be unsupported, or the actively hydrogenating substances and/or their precursors may be applied to supports, such as silicon dioxide or aluminum dioxide, for example.

Preferred catalysts over which the α,β-unsaturated aldehydes are hydrogenated contain 0.3%-15% by mass each of copper and nickel, and also, as activators, 0.05%-3.5% by mass of chromium and advantageously 0.01%-1.6% by mass, preferably 0.02%-1.2% by mass, of an alkali metal component on a support material, preferably aluminum oxide and silicon dioxide. The quantities are based on the catalyst in unreduced state. The alkali metal component is optional.

The catalysts are employed advantageously in a form in which they present a low level of flow resistance, as for example in the form of granules, pellets or shaped bodies, such as tablets, cylinders, extrudates or rings. Advantageously they are activated prior to their use, by being heated in a stream of hydrogen, for example.

The hydrogenation, preferably a liquid-phase hydrogenation, is performed generally under an overall pressure of 0.5 to 20.0 MPa, more particularly of 0.5 to 3.0 MPa, especially 1.5 to 2.5 MPa. Hydrogenation in the gas phase may also be performed at lower pressures, with correspondingly large gas volumes. Where two or more hydrogenation reactors are employed, the overall pressures in the individual reactors may be the same or different within the pressure limits specified.

In the case of hydrogenation in liquid or gaseous phase, the reaction temperatures are generally between 120 and 220° C., more particularly between 140 and 180° C.

Examples of such hydrogenations are described in patent applications EP 0 470 344 and EP 0 326 674.

The hydrogenation of decenals to decanols may optionally be performed in two stages. In this case, in the first stage, over a palladium catalyst, for example, the olefinic double bond is hydrogenated, and in the second stage the carbonyl group is hydrogenated, over one of the catalysts identified above.

Starting from $C_4$ olefins, decanol mixtures are produced which comprise substantially one or more of the following substances:

2-propylheptanol, 4-methyl-2-propylhexanol, 5-methyl-2-propylhexanol, 2-isopropyl-4-methylhexanol, 2-isopropyl-5-methylhexanol. The decanols listed are composed in each case of at least two stereoisomers.

As already mentioned, the composition of these decanol mixtures is dependent on the feedstock and on the hydroformylation process. All decanol mixtures obtained from $C_4$ olefins in the manner described can be used for preparing the esters of the invention. Particularly preferred decanol mixtures are those which consist of 50-99 mol %, more particularly 70-99 mol %, more preferably 85-99 mol %, more particularly 95-99 mol % of 2-propylheptanol.

The synthesis of the isodecyl alcohols from a $C_4$ olefin or $C_4$ olefin mixture is generally more economic than the conventional route via the trimerization of propylene with subsequent hydroformylation and hydrogenation, which produces predominantly methyl-branched isodecanol mixtures. As an alternative, mention may also be made here of the use of $C_{10}$ alcohol mixtures from the Polygas process, which in addition to the $C_{10}$ fractions additionally contain—owing to the use of olefin mixtures having substantially 8 to 10 C atoms as a starting product for the hydroformylation—C9 and C11 alcohols. Nevertheless, these isodecanol mixtures as well are suitable for preparing esters of the invention.

As an example, mention may be made here of the isodecanol mixture from ExxonMobil with the trade name Exxal 10. Furthermore, mixtures of the variants stated above can be used as well for preparing the esters of the invention.

Preferably, the mixtures of isomeric decyl alcohols, particularly those with the formula $C_9H_{19}CH_2OH$ that are used in the process of the invention contain less than 20 mol %, preferably less than 10 mol %, more preferably less than 5 mol %, of decyl alcohols with quaternary C atoms. The presence of these alcohols impairs numerous performance properties and also reduces the rate of biodegradation of the molecule.

It may be advantageous, furthermore, if the isodecanols, preferably those with the formula $C_9H_{19}CH_2OH$, that are used for preparing the diesters of the formula I present in the mixture of the invention contain 1% to 60%, more particularly 1% to 50%, preferably 2% to 30%, of n-decanol. By this means it ought to be possible to improve numerous performance properties such as gelling, plasticizing effect, etc. However, since this alcohol is not formed in significant proportions either by aldol condensation of C5 aldehydes with subsequent hydrogenation, or by the hydroformylation and subsequent hydrogenation of trimer propylene or nonene mixtures from the Polygas process, it would be necessary to admix n-decanol as and when required. N-decanol, in turn, is available industrially, for example, from the oligomerization of ethylene or from the fractionation of fatty alcohols.

The isomer distributions of the isomeric alcohols in the mixtures can be determined using the customary measurement methods familiar to the skilled person, such as NMR spectroscopy, GC or GC/MS spectroscopy, preferably following conversion into the silyl or methyl esters.

Furandicarboxylic Acid

Furan-2,5-dicarboxylic acid (FDCA, CAS No: 3238-40-2) has not hitherto been available on an industrial scale, but can either be prepared as per the literature or acquired commercially. The conversion into the dichloride, which may be desired or preferred, is described at length in the examples.

Esterification

For preparing the esters of the invention, either 2,5-furandicarboxylic acid or a reactive derivative such as the corresponding dichloride, for example (see examples), is reacted with a mixture of isomeric decanols. The esterification takes place preferably starting from furandicarboxylic acid and isodecanol, with the aid of a catalyst.

The esterification of the furandicarboxylic acid with an isodecanol mixture to give the corresponding esters may be carried out autocatalytically or catalytically, with Brønsted or Lewis acids, for example. Irrespective of the type of catalysis selected, there is always a temperature-dependent equilibrium developed between the reactants (acid and alcohol) and the products (ester and water). In order to shift the equilibrium in favor of the ester, an azeotrope former can be used to help remove the water of reaction from the batch. Since the alcohol mixtures used for the esterification boil at a lower temperature than the furandicarboxylic acid, its reactive derivatives, and its esters, and exhibit a miscibility gap with water, they are frequently used as azeotrope former, and can be recycled to the process following removal of water.

The alcohol used to form the ester, or the isomeric decanol mixture which serves simultaneously as azeotrope former, is employed in excess, preferably 5% to 50% by mass, more particularly 10% to 30% by mass of the amount needed to form the ester.

As esterification catalysts it is possible to use acids, such as sulfuric acid, methanesulfonic acid or p-toluenesulfonic acid, for example, or metals or compounds thereof. Suitable examples include tin, titanium, and zirconium, which are used as finely divided metals or usefully in the form of their salts, oxides or soluble organic compounds. In contrast to protic acids, the metal catalysts are high-temperature catalysts which often attain their full activity only at temperatures upward of 180° C. Here, however, it should be borne in mind that the furandicarboxylic acid tends to give off $CO_2$ at temperatures above 190° C., and then the monocarboxylic acid is formed therefrom, and can then naturally no longer be reacted to give the target product. The metal catalysts, however, are preferably used, since in comparison to the proton catalysis they form fewer by-products from the alcohol used, such as olefins, for example. Exemplary representatives of metal catalysts are tin powder, tin(II) oxide, tin(II) oxalate, titanic esters such as tetraisopropyl orthotitanate or tetrabutyl orthotitanate, and zirconium esters such as tetrabutyl zirconate.

The catalyst concentration is dependent on the type of catalyst. In the case of the titanium compounds preferably employed, the concentration is 0.005% to 2.0% by mass, based on the reaction mixture, more particularly 0.01% to 0.5% by mass, especially 0.01% to 0.1% by mass.

The reaction temperatures when using titanium catalysts are between 160° C. and 270° C., preferably 160 to 200° C. The optimum temperatures are dependent on the reactants, reaction progress, and catalyst concentration. They may be easily determined by experiments for each individual case. Higher temperatures increase the reaction rates and promote secondary reactions, such as elimination of water from alcohols or formation of colored by-products, for example. A beneficial fact in relation to the removal of the water of reaction is that the alcohol can be distilled off from the reaction mixture. The desired temperature or desired temperature range can be brought about by the pressure in the reaction vessel. In the case of low-boiling alcohols, therefore, the reaction is carried out at superatmospheric pressure, and at reduced pressure in the case of higher-boiling alcohols. In the case of the reaction of FDCA with a mixture of isomeric decanols, for example, operation takes place in a temperature range from 160° C. to 190° C. in the pressure range from 0.1 MPa to 0.001 MPa.

The quantity of liquid to be recycled to the reaction may consist wholly or partly of alcohol obtained by working up the azeotrope distillate. It is also possible to carry out the workup at a later point in time and to replace some or all of the liquid quantity removed with fresh alcohol, i.e., from an alcohol standing ready in a reservoir vessel.

The crude ester mixtures, which in addition to the ester or esters include alcohol, catalyst or its subsequent products, and optionally by-products, are worked up by conventional methods. This workup encompasses the following steps: removing excess alcohol and, when present, low boilers; neutralizing the acids present; optionally a steam distillation; converting the catalyst into a residue which is easily filterable; removing the solids; and, optionally, drying. The sequence of these steps may differ according to the workup procedure employed.

The mixture of the diisodecyl esters may optionally be separated from the reaction mixture by distillation, optionally after neutralization of the batch.

Transesterification

The diisodecyl esters of the invention can alternatively be obtained by transesterifying a furan-2,5-dicarboxylic diester with an isodecanol mixture. Reactants used are furan-2,5-dicarboxylic diesters whose alkyl radicals attached to the O atom of the ester group have 1-9 C atoms. These radicals may be aliphatic, straight-chain or branched, alicyclic or aromatic. One or more methylene groups in these alkyl radicals may be substituted by oxygen. It is advantageous for the alcohols on which the reactant ester is based to boil at a temperature lower than the isodecanol mixture used. One preferred reactant is dimethyl furan-2,5-dicarboxylate.

The transesterification is carried out catalytically, using Brønsted or Lewis acids or using bases, for example. Irrespective of which catalyst is used, there is always a temperature-dependent equilibrium developed between the reactants (dialkyl ester and isononanol mixture) and the products (diisodecyl ester mixture and alcohol liberated). In order to shift the equilibrium in favor of the diisodecyl ester mixture, the alcohol resulting from the reactant ester is removed from the reaction mixture by distillation.

Here as well it is useful to use the isodecanol mixture in excess. As transesterification catalysts it is possible to use acids, such as sulfuric acid, methanesulfonic acid or p-toluenesulfonic acid, for example, or metals or compounds thereof. Suitable examples include tin, titanium, and zirconium, which are used as finely divided metals or usefully in the form of their salts, oxides or soluble organic compounds. In contrast to protic acids, the metal catalysts are high-temperature catalysts which attain their full activity only at temperatures upward of 180° C. They, however, are preferably used, since in comparison to the proton catalysis they form fewer by-products from the alcohol used, such as olefins, for example. Exemplary representatives of metal catalysts are tin powder, tin(II) oxide, tin(II) oxalate, titanic esters such as tetraisopropyl orthotitanate or tetrabutyl orthotitanate, and zirconium esters such as tetrabutyl zirconate.

In addition it is possible to use basic catalysts, such as oxides, hydroxides, hydrogencarbonates, carbonates or alkoxides of alkali metals or alkaline earth metals, for example. From this group it is preferred to use alkoxides, such as sodium methoxide, for example. Alkoxides may also be prepared in situ from an alkali metal and a decanol and/or an isodecanol mixture.

The catalyst concentration is dependent on the type of catalyst. It is typically between 0.005% to 2.0% by mass, based on the reaction mixture.

The reaction temperatures for the transesterification are typically between 100 and 220° C. They must at least be high enough to allow the alcohol formed from the reactant ester to be removed by distillation at the defined pressure, usually atmospheric pressure, from the reaction mixture.

The transesterification mixtures can be worked up in exactly the same way as described for the esterification mixtures.

Use

The mixtures of isomeric decyl esters of 2,5-furandicarboxylic acid of the invention can be used as plasticizers, especially in plastics compositions, adhesives, sealants, varnishes, paints, plastisols, synthetic leathers, floorcoverings, underbody protection, coated fabrics, wallpapers or inks. The plasticizers of the invention can be used with preference in profiles, gaskets, food packaging, films, toys, medical articles, roofing sheets, synthetic leathers, floorcoverings, underbody protection, coated fabrics, wallpapers, cables and wire sheathing, and with particular preference in food packaging, toys, medical articles, such as in bags and tubes for infusions, dialysis, and drains, for example, wallpapers, floorcoverings, and coated fabrics.

Obtainable using the mixtures of isomeric decyl esters of 2,5-furandicarboxylic acid of the invention are, in particular, compositions of the invention which comprise the mixture of isomeric decyl esters of 2,5-furandicarboxylic acid.

Compositions of this kind may comprise the mixture of isomeric decyl esters of 2,5-furandicarboxylic acid of the invention alone or in mixtures with other plasticizers. Where the compositions of the invention comprise the mixture of isomeric decyl esters of 2,5-furandicarboxylic acid of the invention in a mixture with other plasticizers, the other plasticizers may be selected preferably from the group of the dialkyl phthalates, preferably with 4 to 13 C atoms in the alkyl chain; trialkyl trimellitates, preferably with 4 to 10 C atoms in the side chain; dialkyl adipates and preferably dialkyl terephthalates each preferably with 4 to 13 C atoms in the side chain; 1,2-cyclohexanedicarboxylic alkyl esters, 1,3-cyclohexanedicarboxylic alkyl esters, and 1,4-cyclohexanedicarboxylic alkyl esters, preferably 1,2-cyclohexanedicarboxylic alkyl esters, each preferably with alkyl=alkyl radical having 4 to 13 carbon atoms in the side chain; dibenzoic esters of glycols; alkylsulfonic esters of phenol with preferably an alkyl radical containing 8 to 22 C atoms; polymer plasticizers, glycerol esters, isosorbide esters, and alkyl benzoates, preferably having 7 to 13 C atoms in the alkyl chain. In all cases the alkyl radicals may be linear or branched and also identical or different. With particular preference the composition, in addition to the mixture of isomeric nonyl esters of 2,5-furandicarboxylic acid, comprises, in particular, an alkyl benzoate with alkyl=alkyl radical having 7 to 13 carbon atoms, preferably isononyl benzoate, nonyl benzoate, isodecyl benzoate, propylhelptyl benzoate or decyl benzoate. The fraction of mixtures of isomeric nonyl esters of 2,5-furandicarboxylic acid of the invention in the mixture with other plasticizers is preferably 15% to 90% by mass, more preferably 20% to 80% by mass, and very preferably 30% to 70% by mass, with the mass fractions of all of the plasticizers present adding up to give 100%.

The stated compositions comprising mixtures of isomeric decyl esters of 2,5-furandicarboxylic acid and other plasticizers may be used as a plasticizer composition in plastics compositions, adhesives, sealants, varnishes, paints, plastisols or inks. Examples of plastics products produced from the plasticizer compositions of the invention may include the following: profiles, gaskets, food packaging, films, toys, medical articles, such as are used for infusions, dialysis, and drains, for example, roofing sheets, synthetic leathers, floorcoverings, underbody protection, coated fabrics, wallpapers, cables and wire sheathing. Preferred from this group are food packaging, toys, medical articles, wallpapers, coated fabrics, and floorcoverings.

The compositions of the invention which comprise a mixture of isomeric decyl esters of 2,5-furandicarboxylic acid may comprise a polymer selected from polyvinyl chloride (PVC), polyvinylidene chloride (PVDC), polyacrylates, more particularly polymethyl methacrylate (PMMA), polyalkyl methacrylate (PAMA), fluoropolymers, more particularly polyvinylidene fluoride (PVDF), polytetrafluoroethylene (PTFE), polyvinyl acetate (PVAc), polyvinyl alcohol (PVA), polyvinylacetals, more particularly polyvinylbutyral (PVB), polystyrene polymers, more particularly polystyrene (PS), expandable polystyrene (EPS), acrylonitrile-styrene-acrylate (ASA), styrene-acrylonitrile (SAN), acrylonitrile-butadiene-styrene (ABS), styrene-maleic anhydride copolymer (SMA), styrene-methacrylic acid copolymer, polyolefins, more particularly polyethylene (PE) or polypropylene (PP), thermoplastic polyolefins (TPO), polyethylene-vinyl acetate (EVA), polycarbonates, polyethylene terephthalate (PET), polybutylene terephthalate (PBT), polyoxymethylene (POM), polyamide (PA), polyethylene glycol (PEG), polyurethane (PU), thermoplastic polyurethane (TPU), polysulfides (PSu), biopolymers, more particularly polylactic acid (PLA), polyhydroxybutyral (PHB), polyhydroxyvaleric acid (PHV), polyesters, starch, cellulose and cellulose derivatives, more particularly nitrocellulose (NC), ethylcellulose (EC), cellulose acetate (CA), cellulose acetate/butyrate (CAB), rubber or silicones, and also mixtures or copolymers of the stated polymers or their monomeric units. The compositions of the invention preferably comprise PVC or homopolymers or copolymers based on ethylene, propylene, butadiene, vinyl acetate, glycidyl acrylate, glycidyl methacrylate, methacrylates, acrylates, acrylates or methacrylates having alkyl radicals, attached on the oxygen atom of the ester group, from branched or unbranched alcohols having one to ten carbon atoms, styrene, acrylonitrile or cyclic olefins.

The type of PVC in the composition of the invention is preferably suspension PVC, bulk PVC, microsuspension PVC or emulsion PVC. Based on 100 parts by mass of polymer, the compositions of the invention comprise preferably from 5 to 200, more preferably from 10 to 150, parts by mass of plasticizer.

In addition to the stated constituents, the compositions of the invention may comprise further constituents, more particularly, for example, other plasticizers, fillers, pigments, stabilizers, co-stabilizers such as epoxidized soybean oil, for example, and also lubricants, flowing agents, kickers, antioxidants or biocides.

The compositions comprising the stated polymers may be used as adhesives, sealants, varnishes, paints, plastisols, synthetic leathers, floorcoverings, underbody protection, fabric coatings, wallpapers or inks or for producing same.

Where the stated compositions comprise plastics, they can in particular be processed to profiles, gaskets, one-part or multi-part closure devices, food packaging, films, toys, medical articles, roofing sheets, synthetic leathers, floorcoverings, underbody protection, coated fabrics, wallpapers, cables, and wire sheathing.

The examples which follow are intended to illustrate the invention without restricting its scope of application, which is evident from the description and the claims.

EXAMPLES

The esters of the invention were initially prepared in a two-stage synthesis starting from furan-2,5-dicarboxylic acid via the dichloride.

Example 1

Synthesis procedure for furan-2,5-dicarbonyl dichloride (II)

A 250 ml three-neck flask with reflux condenser and dropping funnel was charged under argon with 72.1 g (462 mmol) of furan-2,5-dicarboxylic acid. Over a period of 10 minutes, 165 g (1.39 mol) of thionyl chloride, to which a few drops of N,N-dimethylformamide were added, were added. The suspension was heated to reflux temperature and the resulting gas was taken off through wash bottles containing aqueous KOH solution. The suspension was then heated for 4 hours under reflux until the evolution of gas was at an end and the dissolution of the solid was complete.

Following removal of excess thionyl chloride, the product was isolated by distillative purification (T=110° C., p=0.0012 MPa).

This gave 79.4 g of dichloride as a colorless crystalline solid (yield 89%) having a melting point: 79.5-80.0° C.

Furan-2,5-dicarbonyl dichloride is stored under inert gas (argon) in the dark at room temperature before being used further.

Example 2

Synthesis of furan-2,5-dicarboxylic esters

Under argon, a three-neck flask with reflux condenser and dropping funnel was charged with the dichloride, which was melted by heating. Added dropwise slowly to the liquid were 2.4 equivalents of alcohol, and an exothermic reaction took place with evolution of gas. The gas produced was passed through wash bottles containing aqueous KOH solution. Following complete addition, the mixture was stirred at a temperature of 80-100° C. for 16 hours.

The excess alcohol was removed under reduced pressure in the presence of boiling chips, and the crude product was purified twice by distillation.

For the synthesis of the comparative example, commercially available 2-ethylhexanol was used. For preparing the ester mixture of the invention, commercially available C10 alcohol with CAS Reg. No. 10042-59-8 was used, as offered, for example, as propylheptanol.

This alcohol had the following composition according to analysis by gas chromatography: 86.3% by mass 2-propylheptanol; 13.4% by mass 2-propyl-4-methylhexanol; 0.3% by mass remainder.

Table 1 below records the results of the two syntheses.

TABLE 1

| Ester | Boiling point of ester | Yield |
|---|---|---|
| Bis(2-ethylhexyl) furan-2,5-dicarboxylate II (comparative example) | 137-138° C. (p = 0.0002 MPa) | 99% |
| Bis(isodecyl) furan-2,5-dicarboxylate (I) (inventive) | 140-165° C. (p = 0.0003 MPa) | 98% |

The conversions of furan-2,5-dicarbonyl dichloride (2) to the corresponding esters are therefore virtually quantitative.

Example 3

Preparation of Plastisols

The advantageous properties achievable with the esters of the invention are to be shown below in plastisols and semi-finished products obtainable from them.

The initial masses used of the components for the various plastisols are indicated in table 2 below.

TABLE 2

Formulas
[all figures in phr (=parts by mass per 100 parts by mass of PVC)]

| | Plastisol formula | | | | |
|---|---|---|---|---|---|
| | 1 | 2 | 3 | 4 | 5 |
| Emulsion PVC (Vestolit B 7021 ultra from Vestolit GmbH) | 100 | 100 | 100 | 100 | 100 |
| Diisodecyl furan-2,5-dicarboxylate I (inventive) | 50 | | | | |
| Di-2-ethylhexyl furan-2,5-dicarboxylate II (comparative example) | | 50 | | | |
| DINP (VESTINOL 9, Evonik Oxeno GmbH, comparative example) | | | 50 | | |
| DPHP (Palatinol 10 P, BASF AG, comparative example) | | | | 50 | |
| Di-2-ethylhexyl terephthalate (Eastman 168 Plasticizer, from Eastman, comparative example) | | | | | 50 |
| Epoxidized soybean oil (Drapex 39, from Chemtura) | 3 | 3 | 3 | 3 | 3 |
| Ca/Zn stabilizer (Mark CZ 149, from Chemtura) | 2 | 2 | 2 | 2 | 2 |

The liquid constituents were weighed out before the solid constituents into a suitable PE beaker. Using a spatula, the mixture was stirred in by hand to leave no unwetted powder. The mixing beaker was then fastened into the clamping device of a dissolver stirrer. The sample was homogenized using the appropriate mixer disk.

The rotary speed of 330 rpm was increased to 2000 rpm, and stirring was continued until the temperature on the digital display of the thermal sensor reached 30.0° C. This ensured that the plastisol was homogenized with a defined energy input. The plastisol thereafter was immediately temperature-conditioned at 25.0° C.

Example 4

Measurement of Gelling Rate

The gelling behavior of the plastisols was investigated in the Physica MCR 101 in oscillation mode, using a plate/plate measuring system (PP25), which was operated under shear rate control. An additional temperature-conditioning hood was fitted to the instrument in order to achieve the best possible heat distribution.

The parameters set were as follows:
Mode: Temperature gradient
Start temperature: 25° C.
End temperature: 180° C.
Heating/cooling rate: 5° C./min
Temperature after measurement: 25° C.
Oscillation frequency: 4-0.1 Hz ramp, logarithmic
Circular frequency omega: 10 1/s
Number of measurement points: 63
Measurement point duration: 0.5 min
Automatic gap adjustment F: 0 N
Constant measurement point duration
Gap width 0.5 mm
Measurement Procedure:

One drop of the plastisol formula under measurement was applied with the spatula, without any air bubbles, to the bottom plate of the measuring system. In the course of this operation it was borne in mind that, after the measuring system has been brought together, some plastisol could swell uniformly out of the measuring system (not more than about 6 mm all round). Then the temperature conditioning hood was positioned over the sample, and measurement was commenced.

The parameter determined was the complex viscosity of the plastisol as a function of the temperature. Onset of the process of gelling was evident from a sudden sharp increase in the complex viscosity. The earlier the onset of this increase in viscosity, the better the gelability of the system.

For a comparison, interpolation of the curves for each plastisol was used to determine the temperature at which a complex viscosity of 1000 Pa·s was reached.

In this procedure, the values obtained are those set out in table 3:

TABLE 3

Gelling behavior

| | Plastisol number from example 3 | | | | |
|---|---|---|---|---|---|
| | 1 (inventive) | 2 (comparative example) | 3 (Comparative example) | 4 (Comparative example) | 5 (Comparative example) |
| Temperature in ° C. at viscosity of 1000 Pa · s | 97 | 80.5 | 88.5 | 114.5 | 99.5 |

It is clearly apparent here that the furan diester of the invention (plastisol 1) exhibits improved gelling as compared with the corresponding phthalate DPHP (plastisol 4) and with the terephthalate DOTP (plastisol 5). The large gap in gelling rate that appears between the two phthalates, DINP and DPHP, is closed by the esters of the invention.

Example 5

Measurement of the Shore Hardness of Castings

Shore hardness A is a measure of the plasticity of a specimen. The further a standardized needle can be made to penetrate into the specimen in a defined measurement time, the lower the measurement value. The plasticizer with the highest efficiency gives the lowest Shore hardness value for a given quantity of plasticizer. Conversely, in the case of highly efficient plasticizers, it is possible to make a certain saving in the proportion in the formula, and in many cases this translates to lower costs for the processor.

For the determination of the Shore hardnesses, the plastisols prepared in accordance with example 4 were poured into circular casting molds having a diameter of 42 mm. The plastisols in the molds were then gelled in a forced-air drying oven at 200° C. for 30 minutes, demolded after cooling, and stored in the drying oven (25° C.) for at least 24 hours prior to measurement. The thickness of the disks was approximately 12 mm.

The measurements themselves were carried out in accordance with DIN 53 505 using a Shore A measuring instrument from Zwick-Roell, the measurement value being read off after 3 seconds in each case. On each specimen, three different measurements were carried out at different points (not in the marginal zone), and the average was recorded in each case.

Table 5 lists the measurement values obtained.

The examples listed demonstrate that the inventive isodecyl ester of the furandicarboxylic acid is virtually equal to DINP and as compared with the corresponding phthalate DPHP and the terephthalate DOTP, has significant improvements in the plasticizing effect.

Example 6

Production of Films from the Plastisols

For producing the test specimens, 1 mm thick films were first of all produced for each formula from Table 3. For this purpose, first of all high-gloss release paper (from Sappi, Italy) was cut to a size of 30*44 cm and placed in the stretcher frame of the LTSV coating apparatus for the Mathis oven. The stretcher frame was then placed on the guide frame, the Mathis oven (type LTF) was set to 200° C., and the frame was preheated for 15 seconds after this temperature had been reached. Thereafter the coating bar was placed into the clamping device, and the coating-bar gap was adjusted, by means of preliminary experiments, in such a way as to produce a film thickness after the end of gelling of 1 mm (+/−0.05 mm). An adhesive strip was mounted on the leading edge of the paper in order to collect excess paste. The paste was then applied ahead of the coating bar, and was coated over the clamped release paper by drawing down the guide frame with the coating bar (at a rate of approximately 6 m/min). The coating bar was then removed, and the adhesive strip with the excess paste was taken off. The melting roll was then lowered, and the stretcher frame was moved into the oven. After gelling (2 minutes at 200° C.), the frame was taken out of the oven again, and the film was peeled from the paper, after cooling.

Example 7

Measurement of the Volatility from the Film

From each of the films produced in Example 6, with a thickness of approximately 1 mm, two circular disks with an area of 50 cm² were produced by punching. The samples were stored at constant humidity in a desiccator with drying gel for at least 24 hours.

TABLE 4

Shore hardnesses

| | Plastisols from example 3 | | | | |
|---|---|---|---|---|---|
| | 1 (inventive) | 2 (comparative example) | 3 (comparative example) | 4 (comparative example) | 5 (comparative example) |
| Shore hardness A | 81 | 75 | 80 | 85 | 83 |

Prior to commencement of the measurement series, a blank sample was subjected to measurement. The results of the blank sample were discarded, since this measurement served only for the warm-up phase of the instrument. The conditioned samples were then placed centrally on a disposable aluminum boat in the Mettler HB43S halogen dryer, and weighed. A standard heating program in the halogen dryer was used for the measurement. The parameters set for this purpose were as follows: the heating rate was adjusted maximally with a linear ramp to 200° C. A time of 10 minutes was fixed for the duration of the experiment. The measurement values (time, temperature, and weight loss) were transmitted every 0.5 min automatically, by means of a data cable, to the evaluation software (Microsoft Excel). At least a duplicate determination was carried out for each sample. If the final results differed by more than 10%, a further determination was carried out. The average values for the weight losses were taken over into a diagram. Each measurement was followed by a period of waiting until the instrument had cooled to below 50° C. again. After that, the next measurement was commenced.

Table 5 lists the mass losses after a time of 10 minutes at 200° C.:

TABLE 5

| | Film from plastisol No. | | | | |
|---|---|---|---|---|---|
| | 1 (inventive) | 2 (comparative example) | 3 (comparative example) | 4 (comparative example) | 5 (comparative example) |
| Mass loss after 10 min in % | 0.88 | 1.88 | 1.12 | 1.02 | 1.02 |

The films produced from the esters of the invention display the lowest volatility.

Accordingly it has been shown that the esters of the invention have a behavior which is superior to that of DOTP and relatively similar to that of DINP. Accordingly it has been possible to achieve the above object through the development of generating, through the development of a plasticizer which is competitive in plastisols as well in relation to DINP and DOTP, an additional utility potential for isodecanols which are rich in 2-propylheptanol.

The invention claimed is:

1. A mixture of isomeric decyl esters of formula (I):

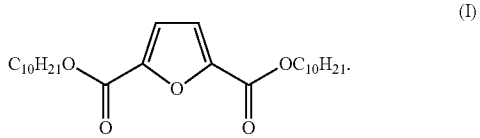

(I)

2. The mixture of claim 1, comprising from 50 to 99 mol % of a 2-propylheptyl radical in a C10 side chain.

3. The mixture of claim 1, comprising less than 20 mol % of C10 side chains comprising quaternary C atoms.

4. A process for preparing the mixture of claim 1, the process comprising: contacting furan-2,5-dicarboxylic acid with a mixture of isomeric C10 alcohols, wherein:
water is liberated;
a molar excess of up to 50% of the isomeric C10 alcohols contacts the dicarbxylic acid; and
a reaction occurs in the presence of at least one catalyst selected from the group consisting of a Brønsted acid and a Lewis acid.

5. A process for preparing the mixture of claim 1, the process comprising:
a) converting furan-2,5-dicarboxylic acid into a corresponding furan-2,5-dicarbonyl chloride;
b) isolating and purifying the corresponding furan-2,5-dicarbonyl chloride to obtain a purified dicarbonyl chloride; and
c) subsequently contacting the purified dicarbonyl chloride with a mixture of isomeric C10 alcohols, wherein hydrogen chloride is released.

6. A process for preparing the mixture of claim 1, the processing comprising: contacting dimethyl furan-2,5-dicarboxylate with a mixture of isomeric C10 alcohols, wherein:
methanol is released; and
a reaction occurs in the presence of at least one catalyst selected from the group consisting of a Brønsted acid a Lewis acid.

7. A composition, comprising the mixture of claim 1 and at least one plasticizer selected from the group consisting of an alkyl benzoate, a dialkyl adipate, a glycerol ester, a trialkyl ester of citric acid, an acylated trialkyl ester of citric acid, a trialkyl trimellitate, a glycol dibenzoate, a dialkyl terephthalate, a dialkyl phthalate, a dialkanoyl ester of isosorbide, a dialkyl ester of 1,4-cyclohexanedicarboxylic acid, a dialkyl ester of 1,2-cyclohexanedicarboxylic acid, and a dialkyl ester of 1,3-cyclohexanedicarboxylic acid.

8. The composition of claim 7, wherein a molar ratio of the isomeric decyl esters to the at least one plasticizer is in a range from 1:15 to 15:1.

9. The composition of claim 7, further comprising at least one polymer selected from the group consisting of polyvinyl chloride, polyvinylbutyral, polylactic acid, polyhydroxybutyral, and polyalkyl methacrylate.

10. A composition, comprising the mixture of claim 1 and at least one polymer selected from the group consisting of a polyvinyl chloride, polyvinylbutyral, polylactic acid, polyhydroxybutyral, and polyalkyl methacrylate.

11. The composition of claim 10, wherein a ratio of the at least one polymer to the isomeric decyl esters is in a range from 30:1 to 1:2.5.

12. A plasticizer, comprising the mixture of claim 1.

13. An article comprising the composition of claim 7, wherein the article is at least one selected from the group consisting of a paint, an ink, an adhesive, an adhesive component, a varnish, a plastisol, and a sealant as a plasticizer.

14. A solvent comprising the composition of claim 7, wherein the solvent is suitable in the preparation of a paint, an ink, an adhesive an adhesive component, a varnish, a plastisol, or a sealant.

15. A lubricating oil component, comprising the composition of claim 7.

16. An auxiliary in metal processing, the auxiliary comprising the composition of claim 7.

17. An article comprising the composition of claim 7, wherein the article is at least one selected from the group consisting of a plastic and a plastic component.

* * * * *